United States Patent [19]

Ohshima et al.

[11] Patent Number: 5,202,507
[45] Date of Patent: Apr. 13, 1993

[54] METHOD FOR DRYING ERYTHRITOL CRYSTALS

[75] Inventors: Yoshikazu Ohshima; Tetsuo Yamada; Yoshimitsu Tanaka, all of Fukuoka, Japan

[73] Assignees: Mitsubishi Kasei Corporation; Nikken Chemicals Co., Ltd., both of Tokyo, Japan

[21] Appl. No.: 904,508

[22] Filed: Jun. 25, 1992

[30] Foreign Application Priority Data

Jul. 30, 1991 [JP] Japan .................. 3-190058

[51] Int. Cl.$^5$ .............................................. C07C 31/22
[52] U.S. Cl. ..................................... 568/868; 568/913
[58] Field of Search ................ 568/868, 913, 916; 435/158

[56] References Cited

U.S. PATENT DOCUMENTS

| 3,035,060 | 6/1957 | Binning et al. | 568/913 |
| 3,308,171 | 5/1965 | Oikawa | 568/868 |
| 5,139,795 | 8/1992 | DuRoss | 568/868 |

FOREIGN PATENT DOCUMENTS 149462  7/1971  Fed. Rep. of Germany .

OTHER PUBLICATIONS

Vogel, Practical Organic Chemistry, Wiley, 1962, pp. 133-139.

Primary Examiner—Marianne M. Cintins
Assistant Examiner—Rebecca Cook
Attorney, Agent, or Firm—Sughrue, Mion, Zinn, Macpeak & Seas

[57] ABSTRACT

A method for drying erythritol crystals having a moisture content of from 1 to 10% by weight to reduce to the moisture content of 0.15% by weight or below, which comprises drying under fluidized state wherein a temperature of a gas to be used in the fluidized drying is controlled within a range of from 10° to 60° C. at least until the moisture content of said crystals is reduced to 0.5% by weight or below.

The moisture content of erythritol crystals (moisture content: 1 to 10% by weight) can be highly efficiently reduced to 0.15% by weight or below in a stable form without deteriorating the crystalline properties and form by fluidized drying said erythritol crystals with the use of a gas flow of a relatively low specific temperature.

9 Claims, No Drawings

METHOD FOR DRYING ERYTHRITOL CRYSTALS

FIELD OF THE INVENTION

This invention relates to a method for drying erythritol crystals. More particularly, it relates to a method for efficiently drying large erythritol crystals having a particle size of from 500 to 700 μm to give a moisture content of 0.15% by weight or below without deteriorating the crystalline properties and form.

BACKGROUND OF THE INVENTION

Erythritol has attracted public attention as a low caloric sweetener having a sweetness of about 0.8 times as much as sucrose. A conventional method for producing erythritol comprises culturing an erythritol-producing microorganism in an aqueous medium containing glucose which is employed as a raw material. After removing cells, culture broth containing the erythritol, thus produced, is purified and the erythritol is crystallized, followed by collecting the erythritol crystals. In usual, the erythritol crystals thus collected should be dried to a low moisture content of 0.15% by weight or below. Since erythritol has a high melting point at 119° C. and a good thermal stability, erythritol crystals are usually hot air-dried so as to achieve a high drying efficiency.

However the conventional method for drying erythritol crystals is disadvantageous in that an extremely long period of time is needed for reducing the moisture content to a desired level and that some portion of the crystals would cohere together during the course of drying and thus the crystalline properties and form are deteriorated. These problems are particularly serious in the case where the erythritol crystals have large particle size of from 500 to 700 μm.

Under these circumstances, the present invention aims at providing a method for efficiently drying erythritol crystals to give a moisture content of 0.15% by weight or below, without deteriorating the crystalline properties and form.

In order to achieve the above-mentioned object, the present inventors have conducted extensive studies. As a result, they have successfully found out that erythritol crystals, even having a large particle size, can be dried to give a moisture content of a desired level without causing any cohesion of the crystals by fluidized drying said crystals with the use of a gas of a temperature controlled to a specific level.

SUMMARY OF THE INVENTION

According to the present invention, there is to provide a method for drying erythritol crystals having a moisture content of from 1 to 10% by weight in order to reduce to 0.15% by weight or below, wherein fluidized drying is employed as a drying process and the temperature of a gas to be used in the fluidized drying is controlled to within a range of from 10 to 60° C. until the moisture content of said crystals is reduced to 0.5% by weight or below.

DETAILED DESCRIPTION OF THE INVENTION

Now the present invention will be described in greater detail.

Erythritol (Meso-erythritol), which is the subject matter of the present invention, is a sugar alcohol having a molecular weight of 122 and represented by a molecular formula of $C_4H_{10}O_4$. Erythritol is represented by the following formula:

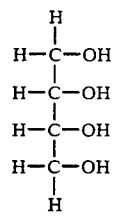

and present as white crystals of a melting point at 119° C. It is closely similar to granulated sucrose in appearance, highly soluble in water, non-digestive and never undergoes browning. Erythritol is widely known as a low caloric sweetener. (Meso-)erythritol can be economically produced by, for example, fermenting glucose or n-paraffin, or oxidizing cellulose or starch followed by hydrogenation and hydrolysis.

The erythritol crystals are usually obtained from culturing an erythritol-producing microorganism in an aqueous medium containing glucose as the raw material under aerobic conditions, purifying the culture broth thus obtained and then crystallizing. The moisture content of these erythritol crystals ranges from 1 to 10% by weight, conventionally from 2 to 8% by weight. The effects of the present invention are particularly remarkable on erythritol crystals of a relatively large particle size of 500 to 700 μm. The methods for producing erythritol per se by culturing an erythritol-producing microorganism have been already known in the arts (refer to, for example, JP-A-63-196298; the term "JP-A" as used herein means an "unexamined published Japanese patent application"). Typical culture conditions therefor are summarized in Table 1 below.

TABLE 1

| Typical conditions for culture method | |
|---|---|
| Erythritol-producing strain: | Aureobasidium SN-G42 |
| Final cell concentration: | 30 to 50 g DCW/l |
| Aqueous medium: | aqua (agitated tank type) |
| Concentration of starting glucose: | 20–50% by weight |
| Culture temperature: | 35–37° C. |
| Culture time: | 4–8 days |
| pH value in system: | 4–7 |
| Additives: | yeast extract, corn steep liquor etc. |
| Content of additives: | 1.5–7% by weight |
| Culture manner: | aeration-agitation |
| Purification: | Removal of cells by solid/liquid separation, followed by treatment with activated carbon, ion exchange resin or chromatography. |
| Composition of treated medium: (% by weight) | erythritol 10–25, glycerol 0.1–2, glucose 0–1, other impurities 1–3 |

The above-mentioned erythritol crystals is required to dry to give a moisture content of 0.15% by weight or below. In the present invention, the drying is essentially performed by fluidized drying. In the present invention that the temperature of a gas to be used in the fluidized drying is essentially controlled within a range of from 10 to 60° C, preferably from 40 to 55° C, at least until the moisture content of the crystal is reduced to 0.5%, preferably 0.15%, by weight or below. That the temperature of the drying gas of higher than the above-mentioned level is undesirable, since the moisture content of the erythritol crystals can be hardly reduced even drying for a long period of time and, furthermore, some portion of the crystals would cohere together so as to form a mass eventually. When the gas temperature is lower than the above-mentioned level, on the other hand, the drying rate becomes low thereby requiring a long time for drying.

The fluidized drying may be performed by a known method wherein a fluidized bed is formed by injecting a large amount of a gas from the underneath of the powder to be treated so as to dry the powder effectively. Examples of the gas usable in the present invention include air and inert gases such as nitrogen gas. In the method of the present invention, the moisture content of the gas is not particularly restricted since the drying rate is not affected thereby. In general, the moisture content of the gas ranges from 0.1 to 4% by weight. The drying time varies depending on, for example, the temperature and flow rate of the drying gas. The drying may be usually carried out for 10 to 20 minutes. The flow rate of the gas may usually range from 0.05 to 2 m³/min.Kg of erythritol, while the linear velocity of the gas may usually range from 0.3 to 1 m/sec.

To further illustrate the present invention in greater detail, the following Examples will be given. It is to be understood, however, that the present invention is not restricted to the description of these Examples but changes and variations may be made without departing from the spirit or scope of the present invention.

EXAMPLES 1 AND 2 AND COMPARATIVE EXAMPLES 1 TO 3

2.0 kg of erythritol crystals obtained by a culture method (moisture content: 3% by weight, average particle size: 500 μm) were fluidized dried in a closed batch-type fluidized drier (Miyamoto Hot Blaster, a product of Miyamoto Seisakusho K.K.) provided with a flow-gas injector at the bottom with the use of air having each temperature as specified in Table 2 below (moisture content 1.5% by weight) at a gas flow rate of 1.5 m³/min and at a gas linear velocity of 0.7 m/sec.

After the completion of the fluidized drying, the moisture content of the erythritol crystals of each case was determined and the cohesion of the crystals was examined. The results are shown in Table 2.

TABLE 2

| | Drying conditions | | Moisture content | |
| | Gas temp.(°C.) | Time (min.) | of erythritol crystals (wt. %) | Cohesion of crystals |
| --- | --- | --- | --- | --- |
| Ex. 1 | 50 | 10 | 0.10 | not appeared |
| Ex. 2 | 40 | 10 | 0.10 | not appeared |
| C. Ex. 1 | 80 | 10 | 0.20 | Partially appeared |
| C. Ex. 2 | 80 | 20 | 0.20 | Partially appeared |
| C. Ex. 3 | 5 | 20 | 1.0 | not appeared |

According to the present invention, erythritol crystals having a moisture content of 1 to 10% by weight can be highly efficiently dried to give a moisture content of a desired level of 0.15% by weight or below with the use of a gas flow at a relatively low specific temperature in a stable state without deteriorating the crystalline properties and form. Although it has not been clarified in detail why the drying with the use of a gas at a low temperature, as done in the present invention, is more effective than the one with the use of a gas at a higher temperature, it is assumed that the gas of a higher temperature would be liable to cause the cohesion of erythritol crystals, which inherently have a high moisture evaporation rate, or solidification at the surface of the same and thus inhibit the evaporation of the moisture remaining inside.

While the invention has been described in detail and with reference to specific embodiments thereof, it will be apparent to one skilled in the art that various changes and modifications can be made therein without departing from the spirit and scope thereof.

What is claimed is:

1. A method for drying erythritol crystals having a moisture content of from 1 to 10% by weight to reduce to the moisture content of 0.15% by weight or below, which comprises drying under fluidized state wherein a temperature of a gas to be used in the fluidized drying is controlled within a range of from 10 to 60° C. at least until the moisture content of said crystals is reduced to 0.5% by weight or below.

2. A method as claimed in claim 1, wherein the particle size of said erythritol crystals is from 500 to 700 μm.

3. A method as claimed in claim 1, wherein the drying is continued until the moisture content of said erythritol crystals is reduced to 0.15% by weight or below.

4. A method as claimed in claim 1, wherein the flow rate of a gas to be used in the fluidized drying is from 0.05 to 2 m³/min.Kg of erythritol.

5. A method as claimed in claim 1, wherein the moisture concentration of a gas to be used in the fluidized drying is from 0.1 to 4% by weight.

6. A method as claimed in claim 1, wherein the linear velocity of a gas to be used in the fluidized drying is from 0.3 to 1 m/sec.

7. A method as claimed in claim 1, wherein the temperature of a gas to be used in the fluidized drying is from 40 to 55° C.

8. A method as claimed in claim 1, wherein a gas to be used in the fluidized drying is an inert gas comprising air or nitrogen gas.

9. A method as claimed in claim 1, wherein said erythritol crystals is obtained by culturing an erythritol-producing microorganism in an aqueous medium containing glucose as a raw material under aerobic conditions, purifying the culture broth thus obtained and crystallizing the erythritol, followed by collecting the same.

* * * * *